United States Patent [19]
Rosenstatter

[11] Patent Number: 6,102,695
[45] Date of Patent: Aug. 15, 2000

[54] DENTISTRY HANDPIECE

[76] Inventor: Otto Rosenstatter, Matzing 105, A-5164 Seeham, Austria

[21] Appl. No.: 09/270,012

[22] Filed: Mar. 16, 1999

[30] Foreign Application Priority Data

Mar. 17, 1998 [AU] Australia ............................ GM 162/98

[51] Int. Cl.[7] ..................................................... A61C 1/00
[52] U.S. Cl. ................................................................ 433/29
[58] Field of Search ........................................ 433/29, 91

[56] References Cited

U.S. PATENT DOCUMENTS

| | | | |
|---|---|---|---|
| 4,484,893 | 11/1984 | Finn | 433/29 |
| 4,519,780 | 5/1985 | Strohmaier et al. | 433/29 |
| 4,858,001 | 8/1989 | Milbank et al. | 358/98 |
| 4,917,603 | 4/1990 | Haack | 433/29 |
| 5,016,098 | 5/1991 | Cooper et al. | 433/29 |
| 5,049,070 | 9/1991 | Ademovic | 433/29 |
| 5,052,924 | 10/1991 | Berg | 433/29 |
| 5,178,536 | 1/1993 | Werly et al. | 433/29 |
| 5,251,025 | 10/1993 | Cooper et al. | 433/29 |
| 5,290,168 | 3/1994 | Cooper et al. | 433/29 |
| 5,634,790 | 6/1997 | Pathmanabhan et al. | 433/29 |
| 5,683,246 | 11/1997 | Coss et al. | 433/29 |
| 5,743,731 | 4/1998 | Lares et al. | 433/29 |

FOREIGN PATENT DOCUMENTS

| | | |
|---|---|---|
| 2208902 | 8/1973 | Germany. |
| 3215189C2 | 10/1983 | Germany. |
| 4009438C2 | 9/1991 | Germany. |
| 19613681A1 | 10/1997 | Germany. |
| 29712789 U 1 | 11/1997 | Germany. |
| 93/05724 | 4/1993 | WIPO. |

*Primary Examiner*—John J. Wilson
*Attorney, Agent, or Firm*—Wenderoth, Lind & Ponack, L.L.P.

[57] ABSTRACT

The present invention is directed to a dentistry handpiece having a handle (1), which is connectable by means of a connector (2) to a supply hose and onto which a tool attachment head (4), carrying tool, is attachable. The handpiece also includes a device having a light conductor (5) for lighting the treatment site, and a device for transmitting an image of the treatment site which includes an image carrier (6) and a converter (10) for converting the image transmitted by the image carrier into electrical signals. The light conductor (5, 31) is arranged in the interior of the handle (1), and the image carrier (6) is arranged on the outside of the handle (1). Preferably, the image carrier is supported on the underside of the handle and is removable therefrom.

11 Claims, 6 Drawing Sheets

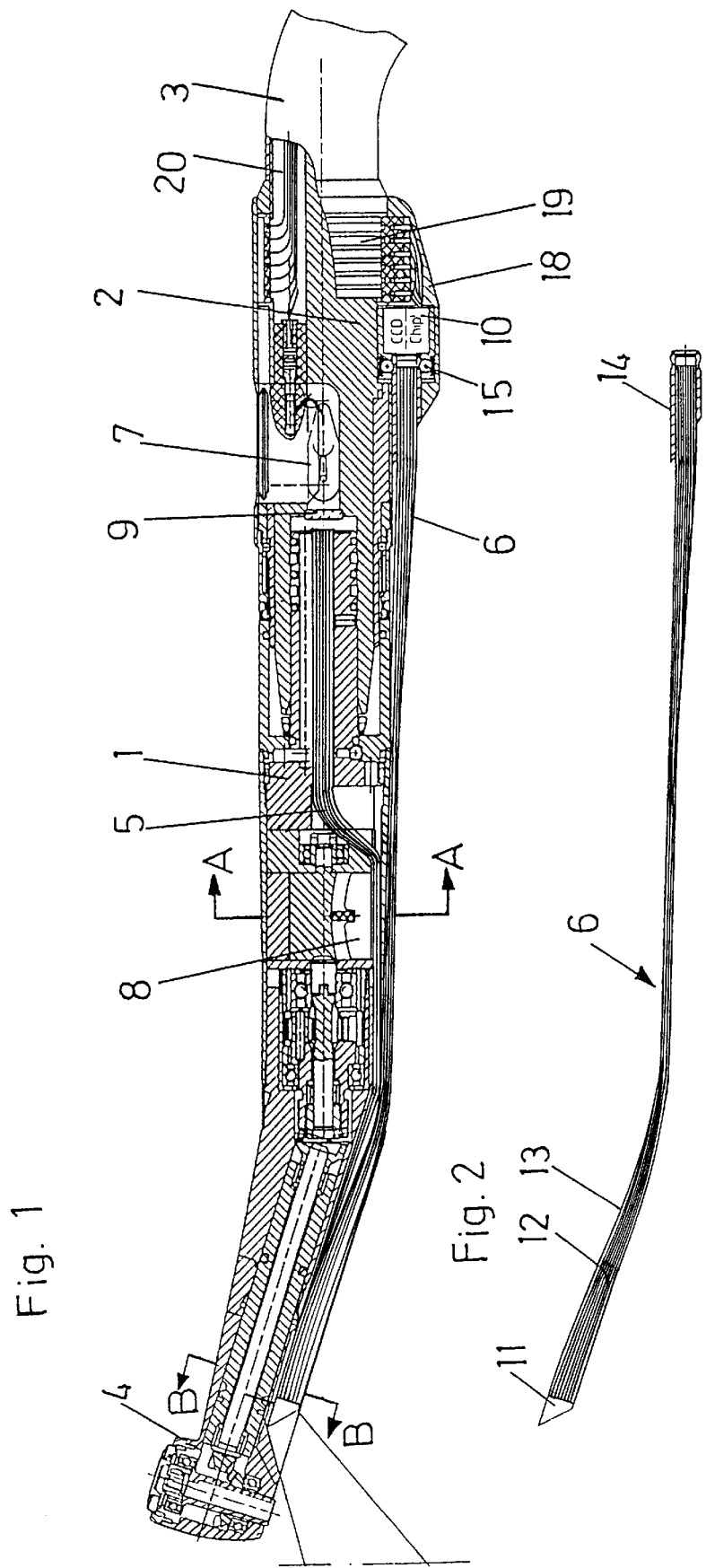

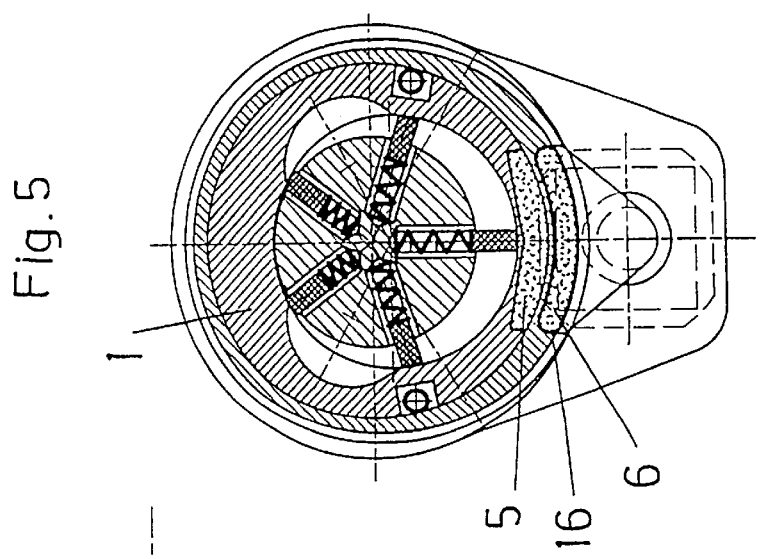
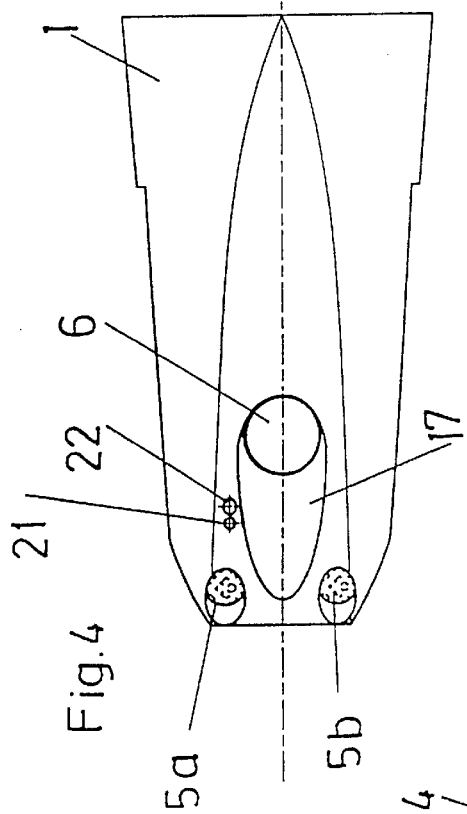
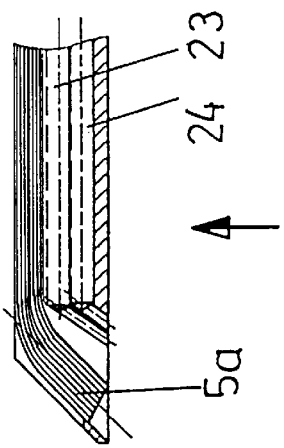
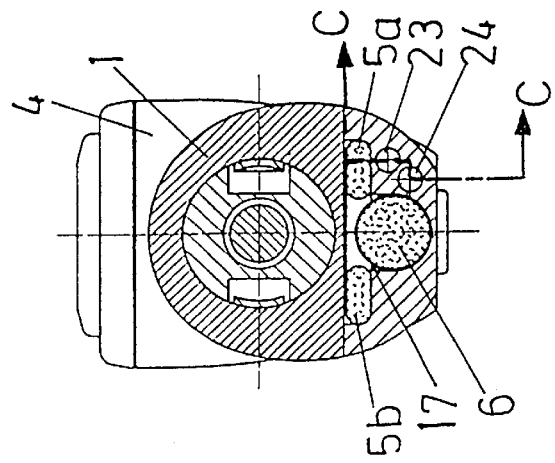

DENTISTRY HANDPIECE

BACKGROUND OF THE INVENTION

The present invention relates to a dentistry handpiece with a handle which can be connected by means of a connector to a supply hose, and upon which a tool attachment head carrying a tool can be fitted, with a means for lighting the treatment site which includes a light conductor, and with a means for transmitting an image of the treatment site which includes an image carrier and a transformer transforming the image transmitted by the image carrier into electrical signals.

Handpieces with an integrated endoscope are known. U.S. Pat. No. 5,049,070 shows such a handpiece, in which an image of the treatment site is transmitted by an image carrier in the form of a glass fiber bundle integrated into the handle of the handpiece to a CCD camera which is arranged in a connector, which connects the handpiece to a supply hose, and which can be uncoupled from the handle. For sterilization of the handpiece in autoclaves, the delicate CCD camera is removed, together with the connector, from the handle.

As the known image carriers are not sufficiently resistant to the hot vapor autoclaving preferably used, however, and at least after prolonged use and frequent autoclaving the image quality is badly impaired, it was proposed in WO 93/5724 to move the light conductor for lighting the treatment site and the image carrier for transmitting an image of the treatment site together to a tube mounted externally on the handpiece and removable therefrom.

SUMMARY OF THE INVENTION

The object of the invention is to further improve the handpiece shown in WO 93/5724 and to make possible a more versatile applicability of such a handpiece.

In accordance with the invention, this is done in that the light conductor is arranged in the interior of the handle, and in that the image carrier is arranged on the outside of the handle, preferably on the underside thereof, and is removable therefrom.

For hot vapor autoclaving of the handpiece according to the invention, the image carrier and the CCD camera can be removed from the handle of the handpiece to be autoclaved, while the light conductor used for lighting the treatment site remains in the handle. Although the quality of the light conductor is impaired to a certain degree by frequent hot vapor autoclaving, the light output transmitted as a whole is impaired by a tolerable extent. Compared to the image conductor, the quality requirements for the light conductor are significantly lower.

By moving the light conductor into the interior of the handpiece, it is further possible to maximize the cross-section of the image carrier, so the image resolution and image quality are improved without the constructional shape of the handpiece increasing. When the endoscopic function of the handpiece is not required, the handpiece can simply be used without the image carrier being mounted on the handle, wherein advantageously in order to conserve the ergonomics of the handpiece, instead of the image carrier a non-functional dummy piece is fitted, which has substantially the same dimensions as the image carrier. Lastly, instead of the image carrier, a suction pipe for suctioning liquid or aerosol from the treatment site can be fitted in the handle, wherein the suction pipe is connected by means of a connecting channel to the suction channel in the connector.

Further advantages and details of the invention will be explained hereinafter with reference to the attached drawings.

BRIEF DESCRIPTION OF THE DRAWINGS

These show, in

FIG. 1 is a longitudinal section through a handpiece according to the invention with an image carrier fitted;

FIG. 2 shows an image carrier removed from the handpiece;

FIG. 4 is a view from below towards the front area of the handle facing the treatment site:

FIG. 5 is a section taken along the line A—A of FIG. 1;

FIG. 6 is a section taken along the line B—B of FIG. 1;

FIG. 7 is a detail of FIG. 6 in a section taken along the line C—C;

DETAILED DESCRIPTION OF THE INVENTION

Figure 3:
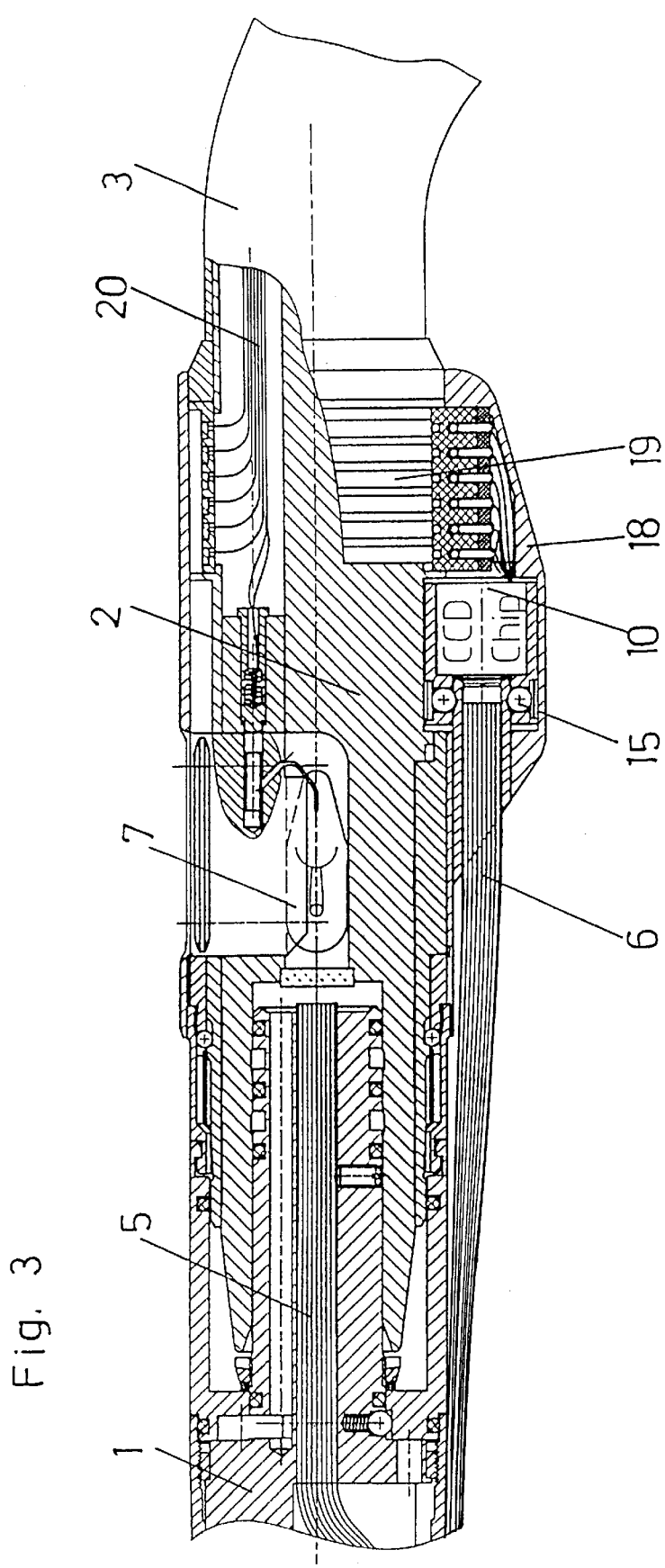
FIG. 3 is an enlarged representation of the rear area of the handpiece of FIG. 1.

The handpiece shown in FIGS. 1 to 7 has a handle 1, which is connected in a rotatable manner to a connector 2 which makes the connection with a supply hose 3. The handle 1 carries on its front side a replaceable tool attachment head 4, in which a tool, not shown in FIG. 1, can be fitted. The drive for this tool is by means of an air-driven blade motor 8 arranged in the handle 1.

For lighting the treatment site, there is arranged in the connector 2 an incandescent lamp 7, the light of which feeds, via a light exit window 9 arranged in the end face of the connector 2, into a light conductor 5 opening out into the end face of the handle opposite the light exit window 9. The light conductor 5 runs within the handle 1 from the rear end thereof to its forward end facing the treatment site. In the rear area of the handle 1, it firstly runs centrally and has a circular cross-section. In the area of the handle 1 in which the blade motor 8 is arranged, it is conducted along the edge area of the handle 1, wherein its cross-section flattens out increasingly, as is shown particularly clearly in FIG. 5. In the forward area of the handle 1, the light conductor 5 divides into two strands 5a and 5b, the front end pieces of which are angled towards the direction of the treatment site and again have a circular cross-section (see FIG. 7). For transmitting an image of the treatment site, there is provided externally on the underside of the handle an image carrier 6, the rear end of which adjoins a CCD camera. In order to receive an image from the direction of the treatment site, the image carrier 6 is provided on its forward end with a prism 11. It would also be possible, however, for the image carrier to terminate with an inclined end surface or, in a similar manner to the light conductor 5, for it to have an end piece angled towards the direction of the treatment site. The image carrier 6 is composed of a glass fiber bundle 12 which is surrounded by a metal sheath 13. In the end area of the image carrier 6 facing towards the CCD camera 10, the metal sheath 13 is additionally surrounded by a coupling piece 14. This cooperates with a catch coupling 15 arranged on the front side of the CCD camera, whereby the image carrier 6 is pressed against the CCD camera.

The image carrier 6 is provided on its two end areas with an approximately circular cross-section, while in its middle area it has an elliptic or flattened cross-section in order to increase the constructional shape of the handpiece as little as possible, as can be seen particularly well from FIG. 5. For fitting the image carrier 6 onto the underside of the handle 1, the handle 1 is provided with a longitudinal groove 16 which, in the front area of the handle 1 facing towards the tool attachment head 4, merges into a receiving channel 17. To fit the image carrier onto the handpiece, the front side of the image carrier 6 is firstly pushed into the receiving channel 17 and then the coupling piece 14 is snapped into the catch coupling 15. The CCD camera 10 and the catch coupling are arranged in a ring 18 which is arranged in a rotatable manner on the connector 2. The electrical signals given out by the CCD camera 10 are transferred from the ring 18 to the connector 2 via collector rings 19 and further conducted via electrical lines 20 leading through the supply hose 3.

As shown in FIG. 4, the strands 5a, 5b of the light conductor 5 open out on either side of the receiving channel 17 for the image carrier 6. Furthermore, outlet apertures 21, 22 for supplying a spray to the treatment site are provided, wherein fluid and air are supplied for producing the sprays through channels 23, 24 (see FIGS. 6, 7).

When the endoscopic function of the handpiece is not being used, the image carrier 6 can simply be removed from the handpiece. In order to preserve the ergonomics of the handpiece, a non-functioning dummy piece (not shown in the Figures) can be fitted instead, which has the same dimensions as the image carrier 6 shown in FIG. 2. The ring 18 with the CCD camera can then remain on the handpiece or be replaced with another ring without a CCD camera.

Figure 8:
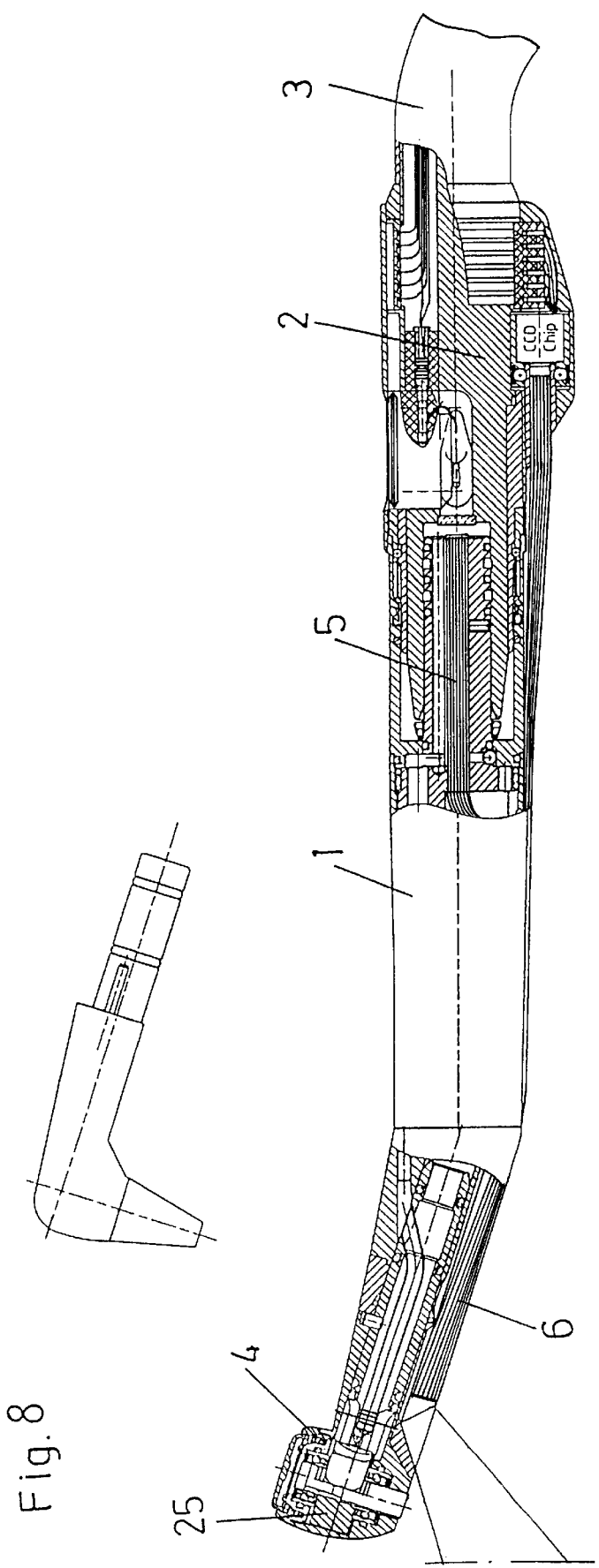
FIGS. 8–10 further embodiments of the handpiece according to the invention.

In the embodiment according to FIG. 8, the driving of the tool is achieved by means of an air-driven turbine 25 arranged in the treatment head. The arrangement of the light conductor 6 and image carrier 6 can then be identical to that shown in FIGS. 1 to 7.

Figure 9:
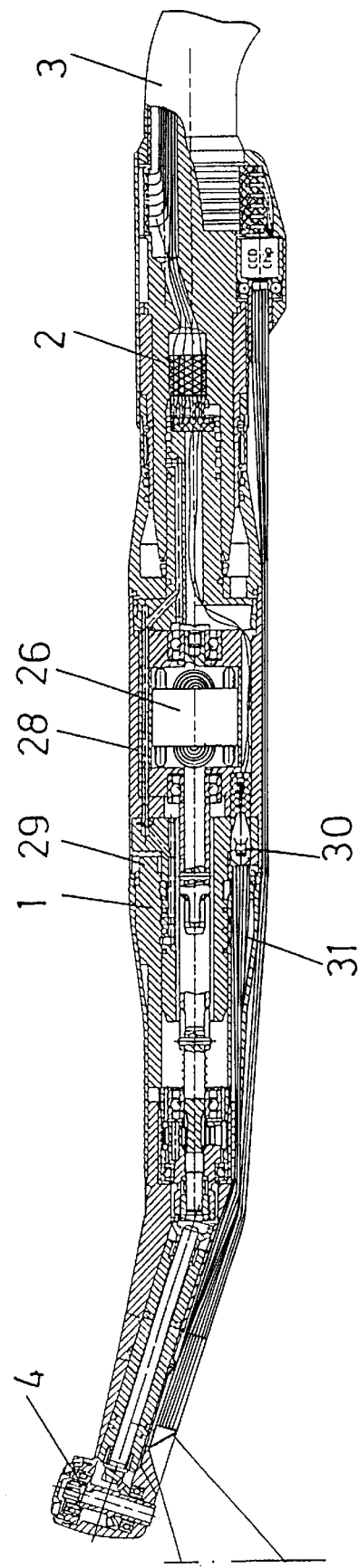
Figure 10:
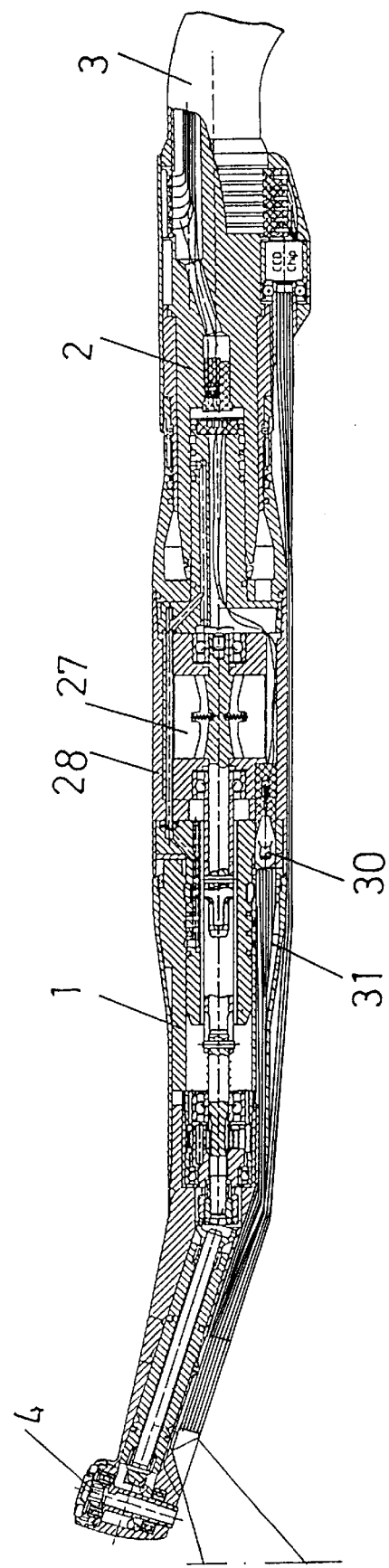

In the handpiece according to FIGS. 9 and 10, a supply shoe is provided which makes possible selective use of an electric motor 26 or an air-driven blade motor 27, and which is connected by means of a locking nose in a rotation-resistant manner to the handle 1. The incandescent lamp 30 is, in this case, arranged in front of the motor 26, 27 on the end face of the supply shoe 28 adjacent to the handle 1, and is opposite to the light conductor 31 adjacent to the end face of the handle 1, and is configured shorter than the light conductor of the embodiment previously described. The arrangement of the image carrier 6 and CCD camera 10 remains unchanged, however.

Figure 11:
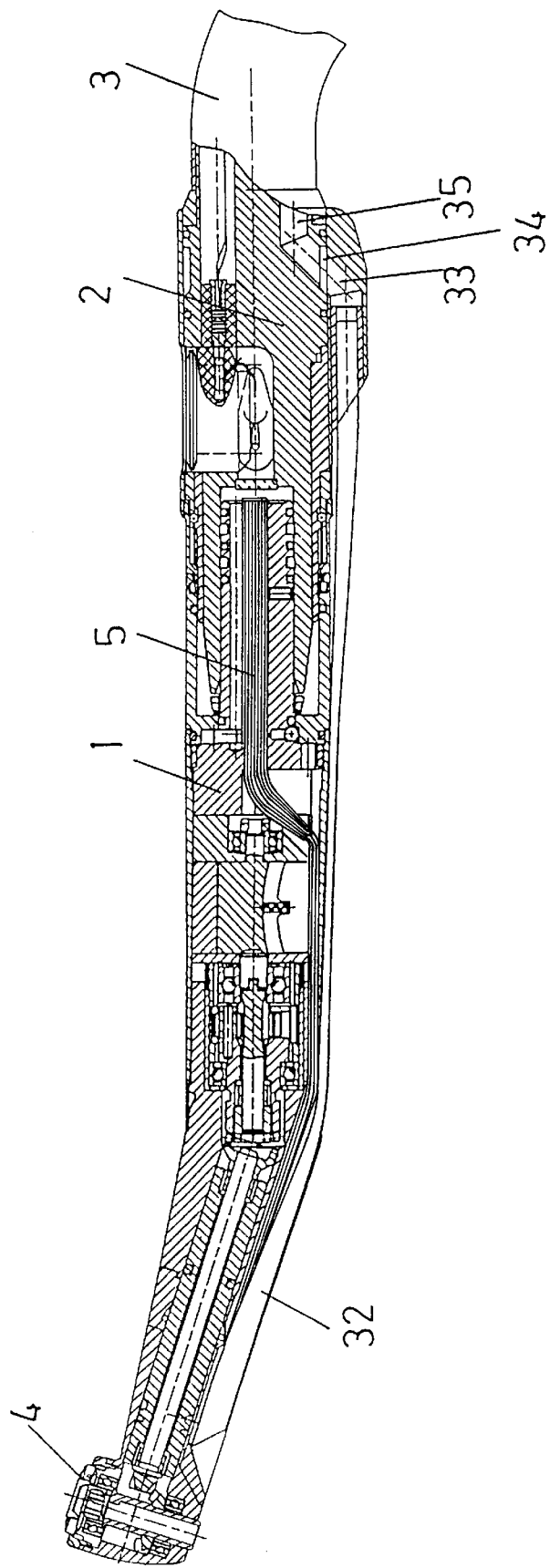
FIG. 11 shows the handpiece according to the invention of FIG. 1 in which the image carrier has been replaced with a suction pipe.

The handpiece shown in FIG. 11 corresponds to the embodiment according to FIGS. 1 to 7, however, the image carrier is removed and replaced with a suction pipe 32 which has the same dimensions as the image carrier 6. This suction pipe consequently fits exactly into the longitudinal groove 16 on the underside of the handle 1, and in the receiving channel 17 arranged on the front end of the handle 1. into which the longitudinal groove 16 merges. At is rearward end, the suction pipe 32 opens out into a connecting channel 33 which connects the suction pipe 32 via an annular channel 34 running externally around the connector 2 to the suction channel 35 running through the connector 2 into the supply hose 3. The connecting channel 33 can then either be arranged on another place on the periphery of the ring 18 shown in FIG. 1 than the CCD camera 10, or the ring 18 with the CCD camera can be replaced with a ring with a connecting channel 33. Furthermore, different connectors 2 could also be provided which can be fitted according to whether the handpiece is to be used with the image carrier 6 or with the suction pipe 32.

The embodiments of the invention shown can also be used with the image carrier fitted for diagnostic purposes without tool attachment heads. For lighting the treatment site, it would also be possible, instead of the arrangement of an incandescent lamp in the hand piece, to supply the light via the supply hose 3 and to transmit it via a light conductor arranged in the connector 2 to the light conductor in the handle 1.

What is claimed is:

1. A dentistry handpiece comprising:

a handle;

a connector for connecting to a supply tube, said connector being connected to a rear end of said handle;

a tool attachment head connected to a front end of said handle;

a lighting device for lighting a treatment site, said lighting device including a light conductor; and an image transmitting device for transmitting an image of the treatment site, said image transmitting device including an image carrier and a converter for converting the image transmitted by said image carrier into electrical signals, wherein said light conductor is arranged in an interior of said handle, and said image carrier is removably supported on an exterior surface of said handle, and wherein said image carrier has a substantially circular cross-sectional shape in an area of its front and rear ends, while its cross-sectional shape in an intermediate area is at least twice as wide as it is high.

2. The dentistry handpiece as claimed in claim 1, wherein said image carrier is arranged on an underside of said handle.

3. The dentistry handpiece as claimed in claim 1, wherein an underside of said handle has a longitudinal groove for removably receiving said image carrier.

4. The dentistry handpiece as claimed in claim 3, wherein said longitudinal groove merges into a receiving channel for receiving said image carrier at a front area of said handle facing said tool attachment head.

5. The dentistry handpiece as claimed in claim 1, wherein said image carrier comprises a glass fiber bundle surrounded by a sleeve.

6. The dentistry handpiece as claimed in claim 1, wherein said converter is arranged on an exterior surface of said connector and is removable therefrom.

7. The dentistry handpiece as claimed in claim 6, wherein said handle and said converter are rotatable with respect to said connector.

8. The dentistry handpiece as claimed in claim 7, wherein said converter is arranged in a ring that is rotatable with respect to said connector, said converter having a catch coupling which cooperates with said image carrier in order to press said image carrier against said converter.

9. The dentistry handpiece as claimed in claim 1, further comprising a dummy piece which can be removably connected to said to said handle, said dummy piece being capable of replacing said image carrier so that said handpiece can be used without said image carrier, wherein said dummy piece is substantially the same size as said image carrier.

10. The dentistry handpiece as claimed in claim 1, further comprising a suction pipe which can be fitted to said handle in place of said image carrier, wherein said suction pipe is substantially the same size as said image carrier in an area in which said suction pipe runs along said handle.

11. The dentistry handpiece as claimed in claim 10, further comprising a part arranged on said connector, said part having a connecting channel for connecting said suction pipe to a suction channel in said connector.

* * * * *